United States Patent
Petrich et al.

(10) Patent No.: US 8,293,539 B2
(45) Date of Patent: Oct. 23, 2012

(54) ANALYSIS SYSTEM WITH CODING RECOGNITION

(75) Inventors: Wolfgang Petrich, Bad Schoenborn (DE); Stefan Kalveram, Viernheim (DE); Markus Serr, Speyer (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 5 days.

(21) Appl. No.: 13/021,356

(22) Filed: Feb. 4, 2011

(65) Prior Publication Data

US 2012/0045842 A1 Feb. 23, 2012

Related U.S. Application Data

(63) Continuation of application No. PCT/EP2009/060044, filed on Aug. 3, 2009.

(30) Foreign Application Priority Data

Aug. 4, 2008 (EP) ..................... 08161755

(51) Int. Cl.
*G01N 33/50* (2006.01)
*G01N 33/66* (2006.01)
*G01N 21/75* (2006.01)

(52) U.S. Cl. .............. 436/169; 436/44; 436/46; 436/95; 436/164; 422/420; 422/66; 422/68.1; 422/82.05; 435/14; 435/287.7; 435/288.7

(58) Field of Classification Search ............. 436/14, 436/44, 46, 63, 95, 164, 169; 422/420, 430, 422/66, 68.1, 82.05, 82.09, 421; 435/14, 435/287.7, 288.7

See application file for complete search history.

(56) References Cited

U.S. PATENT DOCUMENTS

| | | | |
|---|---|---|---|
| 5,077,010 A | 12/1991 | Ishizaka et al. | |
| 5,281,395 A | 1/1994 | Markart et al. | |
| 5,846,838 A | 12/1998 | Chandler | |
| 5,902,982 A | 5/1999 | Lappe | |
| 5,945,341 A * | 8/1999 | Howard, III | 436/46 |
| 6,036,919 A | 3/2000 | Thym et al. | |
| 6,168,957 B1 * | 1/2001 | Matzinger et al. | 436/518 |
| 6,335,203 B1 | 1/2002 | Patel et al. | |
| 7,586,590 B2 * | 9/2009 | Baskeyfield et al. | 356/42 |
| 2002/0132363 A1 * | 9/2002 | Rehm | 436/164 |
| 2003/0185707 A1 | 10/2003 | Iwaki et al. | |
| 2004/0233339 A1 | 11/2004 | Elliott | |
| 2005/0163657 A1 * | 7/2005 | Childers et al. | 422/50 |

(Continued)

FOREIGN PATENT DOCUMENTS

CA 2311496 A1 6/1999

(Continued)

*Primary Examiner* — Maureen Wallenhorst
(74) *Attorney, Agent, or Firm* — Krieg DeVault LLP

(57) ABSTRACT

An analysis system for detecting at least one analyte in a sample is proposed, in particular for detecting glucose in a bodily fluid. The analysis system is designed to detect the analyte using at least one test element. The test element has at least one analysis zone for detecting the analyte. The test element includes at least one coding with at least one test element specific item of information and/or at least one position specific item of information. The analysis system includes a detector and furthermore at least one transfer device which is designed to afford the detector the possibility of acquiring the analysis zone in at least a first position and to afford the detector the possibility of acquiring the coding in at least a second position which differs from the first position.

19 Claims, 6 Drawing Sheets

U.S. PATENT DOCUMENTS

| | | |
|---|---|---|
| 2006/0002816 A1 | 1/2006 | Zimmer et al. |
| 2006/0173380 A1 | 8/2006 | Hoenes et al. |
| 2006/0216817 A1 | 9/2006 | Hoenes et al. |
| 2007/0015286 A1* | 1/2007 | Neel et al. .................. 436/149 |
| 2007/0020143 A1 | 1/2007 | Seidenstricker et al. |
| 2007/0273928 A1 | 11/2007 | Robinson et al. |
| 2008/0105024 A1 | 5/2008 | Creaven et al. |
| 2009/0116015 A1 | 5/2009 | Petrich et al. |
| 2009/0223287 A1* | 9/2009 | Dai et al. .................... 73/64.56 |
| 2010/0012490 A1* | 1/2010 | Hsu .............................. 204/400 |
| 2011/0111522 A1* | 5/2011 | Zimmerie et al. ............ 436/501 |

FOREIGN PATENT DOCUMENTS

| | | |
|---|---|---|
| DE | 10332488 A1 | 2/2005 |
| DE | 10343896 A1 | 4/2005 |
| EP | 0646784 B1 | 11/2003 |
| EP | 1424040 A1 | 6/2004 |
| EP | 0837320 B1 | 3/2006 |
| EP | 1739432 A1 | 1/2007 |
| EP | 1843148 A1 | 10/2007 |
| WO | 97/02487 A1 | 1/1997 |
| WO | 2004/056269 A1 | 7/2004 |

* cited by examiner

ANALYSIS SYSTEM WITH CODING RECOGNITION

CLAIM OF PRIORITY

The present application is a continuation application based on and claiming priority to PCT/EP2009/060044, filed Aug. 3, 2009, which itself claims the priority filing benefit of European Application No. 08161755.7, filed Aug. 4, 2008, each of which are hereby incorporated herein by reference in their respective entireties.

TECHNICAL FIELD OF THE INVENTION

The present application relates to an analysis system and a method for detecting at least one analyte in a sample. Such analysis systems and methods can be used in particular for qualitative and/or quantitative detection of analytes in liquid samples, in particular bodily fluids such as interstitial fluid, blood or urine. In particular, the analysis system and the method can be used for detecting glucose and/or other metabolites. The following description focuses on the use of the invention within the scope of diabetes diagnostics; however, other areas of application are also feasible.

BACKGROUND

In clinical diagnostics, the examination of blood samples or other samples of a bodily fluid, for example the interstitial fluid, affords the possibility of early and reliable detection of pathological states and the targeted and founded monitoring of body states. Medical diagnostics generally presuppose obtaining a blood or interstitial fluid sample from the patient to be examined. To this end, the skin is usually perforated, for example at the finger pulp or the ear lobe, using a sterile, pointy or sharp lancet in order to obtain a few microliters or less of blood for the analysis.

These days, the self-determination of blood glucose is a method of diabetes monitoring applied worldwide. Blood glucose equipment in the prior art generally has analysis equipment into which a test element (e.g. a test strip and/or a test tape) is inserted. The sample to be analyzed is applied to a test field (also referred to as an analysis zone in the following text) of the test element and possibly reacts in the test field with one or more reagents which are generally selected specifically for the analyte to be detected. By way of example, the reaction can be detected in an optical, in particular photometric, and/or electrochemical fashion.

For said evaluation, the prior art discloses different forms of test elements and test equipment which can be used or modified for the purpose of the present invention. It is possible to refer in particular to the detection reagents illustrated in these documents for the purpose of the present invention. By way of example, it is possible to use strip-like test elements as are described, for example, in the documents CA 2311496 A1, U.S. Pat. No. 5,846,838 A, U.S. Pat. No. 6,036,919 A or WO 97/02487, the disclosures of each of which are hereby incorporated by reference in their respective entireties. Test tapes, with a multiplicity of test fields or analysis zones positioned in series on a tape that is then wound up in a cassette and provided for use in analysis equipment, are further multilayered test elements known from the prior art. Such cassettes and analysis tapes are described, for example, in the documents DE 10332488 A1, DE 10343896 A1, EP 1 424 040 A1, WO 2004/056269 A1 and US 2006/0002816 A1, the disclosures of each of which are hereby incorporated by reference in their respective entireties.

However, when using test elements in practice, a number of technical problems occur which have to be overcome in many cases by complex instrumental solutions. For example, it is a problem that various test elements which can be used in an analysis system can have differences between them. For example, differences can emerge regarding the manufacturer and/or the manufacturing process, regarding the detection reagents used, regarding the analyte to be detected, regarding the analysis method and/or analysis system to be used, regarding the conditions in which the analysis is to be carried out, regarding the parameters and/or the algorithms for evaluating measurements, regarding the lot numbers, regarding lot-specific peculiarities, regarding the production process, regarding the number of analysis zones on a test element or the like. Such test element specific information or analysis zone specific information will also be referred to as "test element specific information" in the following text, with this term intending to comprise general information relating to a test element and/or an analysis zone of the test element and which can accordingly change from test element to test element, or even within a test element, for example from analysis zone to analysis zone. This can also comprise other information than that mentioned above.

Since manual input of such test element specific information is generally unacceptable or difficult for the patient, the prior art discloses various systems in which such test element specific information can be read automatically. Hence, for example, systems are known in which a calibration test element must first of all be entered into the analysis system. See, for example, US 2007/0273928 A1, the disclosure of which is hereby incorporated by reference herein in its entirety. Also known are systems in which a separate evaluation code is provided on the test elements and which is read by a separate reading unit. See, for example, U.S. Pat. No. 5,281,395, the disclosure of which is hereby incorporated by reference herein in its entirety. In addition to such code systems for individual test strips, codings for test tapes are also known in which a coding region on the test tape is provided at the beginning of a test tape, the former comprising at least one item of information. This coding region can, for example, be read by the detector which is also used for the optical measurement. See, for example, U.S. Pat. No. 5,077,010, the disclosure of which is hereby incorporated by reference herein in its entirety.

In addition to the test element specific information, the correct positioning of the test elements in the analysis systems also plays an important role in many cases. Additional sensors which monitor a correct positioning of the test elements are generally provided for this purpose. One example of such positioning employs a separate orientation field on the test element which can be used to determine whether the test strip was inserted into the analysis system correctly or upside down. See, for example, U.S. Pat. No. 6,335,203 B1, the disclosure of which is hereby incorporated by reference herein in its entirety.

However, the analysis systems disclosed in the prior art are in many cases afflicted with disadvantages for practical use, which in particular substantially increase the instrumental complexity of such systems. Thus, in many cases, as illustrated above, a separate sensor system is required for acquiring the test element specific information and/or for acquiring the tape positioning. Such a sensor system means additional complexity in terms of hardware and software, which increases the production costs of the analysis systems and can also significantly increase the weight and the installation space of such systems, which play an important role in the practical use in the daily diagnosis.

It is therefore an object of the present invention to provide an analysis system and a method for detecting at least one analyte in a sample which, at least as far as possible, avoids the disadvantages of the systems and methods known from the prior art. In particular, the instrumental complexity is intended to be decreased, and a system with a small installation space and a low weight is intended to be provided.

SUMMARY

This object and others that will be appreciated by a person of ordinary skill in the art have been achieved according to the embodiments of the present invention disclosed herein. The proposed method can be realized in one of the illustrated embodiments by using an analysis system according to the present invention, and the analysis system can be designed to implement a method according to the present invention in accordance with one of the described embodiments so that it is possible to refer to possible refinements of the method for possible refinements of the analysis system, and vice versa.

The proposed analysis system and the proposed method are used for the purpose of detecting at least one analyte in a sample, for example for detecting glucose in a bodily fluid. To this end, reference can be made in general terms to the extensive prior art relating to analyte detection that a person of ordinary skill in the art will understand and appreciate.

In analyte detection systems and methods relevant to the present invention, the analyte is detected by using at least one test element. In particular, the detection can be effected, as described above, optically, for example by using reflectometric and/or colorimetric methods. For this purpose, the analysis system can, for example, comprise a control which undertakes an evaluation of the measurement by using measurement results determined by a detector, for example by using one or more data processing devices, in particular microprocessors. In the process, the analyte can be detected qualitatively or else quantitatively.

The test element comprises at least one analysis zone for detecting the at least one analyte. By way of example, this analysis zone can be applied in the form of at least one test field on the test strip and/or the test tape and can comprise at least one test chemical which reacts specifically to the analyte to be detected. By way of example, this reaction, as illustrated above, can comprise a color reaction. In addition to the at least one analysis zone, the test element can furthermore comprise other elements, for example a lancet for generating a sample of the bodily fluid in accordance with the above description. By way of example, analysis zones and lancets can be arranged alternately on a test tape.

In principle, the present invention can be employed in connection with a multiplicity of test elements, for example with test elements known from the prior art. Thus, the test element can for example comprise one or more of the following test elements: a test strip, in particular an individual test strip with an individual analysis zone or a multiplicity thereof; a test tape; a test wheel with a multiplicity of analysis zones radially arranged about the circumference; a test wheel with a multiplicity of analysis zones arranged on its surface, in particular analysis zones which are arranged in a cake-slice shape; a foldable test element with a multiplicity of analysis zones (fan folding). By way of example, in this case it is possible to use test elements in which the sample is directly applied onto the analysis zone, for example by direct dropping, dabbing or the like. This direct application can for example be effected by "top dosing", in which the analysis zone is for example arranged on a flat surface of the test element and the sample acts on it from above. However, alternatively or additionally, so-called "edge dosing" would also be possible, in which the sample acts on an end face or side face of the test element. In the case of edge dosing, it is possible, for example, to apply the sample directly onto the analysis zone, or to effect a transport of the sample from the application location to the analysis zone, for example by means of capillary forces. Further refinements are feasible. There is also a multiplicity of possibilities regarding the type of detection of the analyte. Thus, for example, electrochemical detection is possible. Alternatively, or additionally, an optical detection can be effected. By way of example, in the latter case, a direct optical detection can be effected by irradiation with light. Alternatively, or additionally, the irradiated light or the light emitted by the analysis zone can also be transported by one or more optical waveguides. Various other refinements are feasible.

The test element furthermore comprises at least one coding with at least one test element specific item of information and/or at least one position specific item of information. Reference can in this case be made to the above description of the prior art for the definition and for examples of the term "test element specific information". In particular, the test element specific item of information can comprise at least one item of information which characterizes the test element and/or an analysis zone of the test element. The test element specific item of information can in this case relate to individual, a number of or all analysis zones of the test element. Here, a position specific item of information is understood to be an item of information which characterizes a position on the test element. This can for example be an item of information about a location on a test tape. The position specific item of information can for example be contained wholly or partly in at least one positioning marker which is a component of the coding.

A basic idea of the present invention is to also simultaneously use a detector of the analysis system, which is used for evaluating the measurement by means of the analysis zone, for a number of additional functions. According to the invention, the detector is used to also acquire the coding, wholly or partly, in addition to acquiring the analysis zone. Hence, the detector can for example be used to acquire the at least one test element specific item of information. Alternatively, or additionally, the detector can also be used to acquire the at least one position specific item of information.

In the general case of a test element, the test element specific item of information or the position specific item of information or both types of information of the coding can in principle be acquired by the detector.

If the test element is a test strip, the invention proposes that the detector acquires at least the test element specific item of information of the coding. In this case, additional information can also be acquired by the detector, for example a positioning of the test strip in the analysis system, for example whether the test strip was correctly inserted into the analysis system and/or whether the test strip was inserted into the analysis system with the correct orientation. To this end, the at least one position specific item of information can for example be additionally acquired by the detector.

This aspect of the invention allows for the fact that, in general, position specific information plays a secondary role in test strips. In this case, the acquisition of the at least one test element specific item of information is more important. In this respect, the coding comprises at least the test element specific item of information in the case of test strips. Nevertheless, even in the case of test strips, it is possible to additionally acquire at least one position specific item of information.

By contrast, if the test element is a test tape, the invention proposes that at least the position specific item of information is acquired by the detector. The analysis system can then be designed to also use this position specific item of information acquired by the detector to position the test tape. In this respect, it is proposed that if the test element is a test tape, the coding comprises at least the position specific item of information. This aspect of the invention allows for that fact that, in many cases, the positioning plays a decisive role in test tapes in contrast to, for example, individual test strips. Nevertheless, even in the case of a test tape, the coding can naturally also contain a test element specific item of information which can additionally be read by the detector.

Naturally, the detector can also comprise a multiplicity of individual detectors, for example of detectors for different spectral ranges. However, in this case, all individual detectors, or at least one of the individual detectors, simultaneously undertake the objects described above, that is to say they are used in a multifunctional fashion.

In accordance with this idea of the invention, it is thus proposed that the analysis system comprises a detector which is used in multifunctional fashion. The analysis system comprises at least one transfer device which is designed to afford the detector the possibility of acquiring the analysis zone in at least a first position and to afford the same detector the possibility of acquiring the coding in at least a second position, which differs from the first position.

Hence, the at least one transfer device affords the possibility of the detector acquiring the analysis zone in the first position and acquiring the coding in the at least one second position. This can be effected in different ways. For example, the transfer device can be designed to position the test element relative to the detector, or vice versa. Mixed forms, in which positioning of both the detector and the test element are undertaken, are also possible. Here, the transfer does not necessarily have to be effected actively, that is to say by the analysis system effecting a force (for example by means of a suitable positioning actuator), but said analysis system can for example also only passively provide the possibility of such a transfer, with it being possible for the actual transfer to be undertaken by a patient as well, for example. The latter can, for example, be effected by a guide in which the test element can be moved laterally by manual means and/or by drive elements (such as clamps, gearwheels, driving rods or the like) acting thereon. The coding arranged on the test element can be guided past the detector during this lateral movement. Instead of an individual first position and an individual second position, provision can also be made for a plurality of such first positions and/or for a plurality of such second positions. In particular, the coding, as illustrated above, can be of a multipart design, it being possible for these multiple parts of the coding to be read in different positions. Thus, the coding can for example comprise the test element specific item of information and the position specific item of information at different locations. By way of example, in this case, two second positions can be provided: one for acquiring the test element specific item of information and one for acquiring the position specific item of information. Various refinements are feasible.

In the process, the test element does not necessarily have to remain in the first position and/or the second position, but can also only be guided past the detector. Here, the designation "first position" and "second position" contains no statement about a sequence of acquiring the analysis zone and the coding by the detector, but is only intended to label and differentiate between these positions. Thus, for example, the analysis zone can be acquired first, followed by acquiring the coding, or vice versa. An at least in part temporally overlapping acquisition is also feasible, for example if the detector has an acquisition field (for example, an image region of a camera) in which the analysis zone and the coding can be arranged and acquired one after the other and/or temporally overlapping, at least in part.

Hence, in the case of a test strip, the proposed analysis system differs from known analysis systems in that the detector is used in a multifunctional fashion to also acquire the coding with the at least one test element specific item of information and/or the at least one position specific item of information. This makes it possible to save significant amounts of installation space and reduce instrumental complexity. In this case, the test strip can be a test strip with a flexible and/or rigid, substantially flat carrier, for example a test strip with a carrier made of plastic, paper, ceramics or a combination of these and/or other materials.

In the case of a test tape, it is possible, in principle, to use all types of test tapes as are, for example, also known from the prior art. These test tapes can also, for example, again have a tape-shaped carrier, for example a carrier in the form of a plastic tape, a paper tape or a laminate tape. Other types of elongate carriers, such as chains, threads or the like, are also possible. When using test tapes, the proposed analysis system differs from known analysis systems particularly in that at least the position specific item of information is also acquired in addition to the acquisition of the analysis zones. In the process, the analysis system can be designed to also use the coding acquired by the detector, or the position specific item of information, to position the test tape. To this end, the coding, for example, can be acquired by means of a suitable control when the test element is arranged in the second position. This acquisition can, for example, comprise acquiring one or more positioning markers, for example positioning strips, positioning crosses or the like. Additionally, in this case it is also possible to acquire at least one test element specific item of information of the coding.

Starting from this recognition of the positioning, the control can then be designed, for example in program-technical terms, to position the test tape in a next step such that the analysis zone is positioned in front of the detector. In practice, this positioning is frequently also referred to as a "start/stop" pulse. Starting from acquiring the coding, the control for example recognizes that continued spooling of the test tape by a predetermined amount (for example, by a predetermined tape distance or a predetermined spool time at a known spool speed) is required to position an analysis zone in front of the detector.

The latter is particularly advantageous if test elements or test tapes are used in which at least one individual coding is assigned to each analysis zone or to a group of analysis zones. By way of example, analysis zones and codings can be arranged alternately on the test element. Here, it is possible for even a multiplicity of analysis zones to be arranged across the tape direction of the test tape, for example, and form a group, for example a group of analysis zones which can simultaneously be wetted by the sample. A common coding can be assigned to these analysis zones. As an alternative, or in addition, to a common coding for the entire test tape, it is also possible that in each case provision is made for at least one separate coding for an analysis zone or a group of analysis zones which can simultaneously be acted upon with a sample and hence be used simultaneously in the analysis. By way of example, this group can also be simultaneously acquired by the detector.

In this respect, the proposed analysis system also differs significantly from known analysis systems because, in particular, a separate positioning sensor, which generates a start/stop pulse in known systems, can be dispensed with. Hence, the combination of the functionalities of acquiring the analysis zone, the test element specific information and/or the position specific item of information in turn means a reduction in the instrumental complexity, a save in costs and a reduction of installation space and weight of the analysis systems.

The analysis system can furthermore comprise an evaluation unit which can also, wholly or in part, be component-identical with the mentioned control. This evaluation unit can in particular be designed to detect the analyte using the acquired test element specific item of information. To this end, the evaluation unit can, for example, as explained above in the context of the control, comprise one or more pieces of data processing equipment, for example a microprocessor. Furthermore, provision can be made for input and output means in order to transfer the results of the evaluation of the detection of the analyte, for example, to a user and/or to a different piece of equipment, for example a graphical input/output means, interfaces, keyboards or the like.

In one embodiment, the detector comprises an optical detector. In one refinement, the detector comprises a spatially resolving detector. The spatial resolution can be implemented in a number of ways which can also be combined. By way of example, an illumination of the detector can thus be designed as a spatially resolving illumination which, for example, scans different regions of the analysis zone one after the other in order to ensure a spatially resolving detection. Alternatively, or additionally, it is also possible to use a spatially resolving optical system, for example a scanning optical system, by means of which the different regions of the analysis zone can be scanned one after the other. Again alternatively, or additionally, the image sensor can also be designed as a spatially resolving image sensor. By way of example, the detector can comprise an image sensor, in particular a CCD or CMOS image sensor chip, for the spatially resolved recording of image information.

Such spatially resolving records of image information can be used independently of the type of spatial resolution to evaluate analysis zones and hence improve the accuracy of the detection of the at least one analyte. See, for example, EP 1 843 148 A1. By way of example, gray value information acquired by the spatially resolving optical detector can to this end also be evaluated by means of histogram analysis. As is explained in more detail below, the evaluation of spatially resolved image information also affords the possibility of evaluating two-dimensional optical codings in addition to one-dimensional codings. In general, at least a partial evaluation of the coding (for example regarding the test element specific information and/or the spatial information for positioning the test tape contained therein) can also in part be effected in the detector itself, for example in the CCD or CMOS image sensor chip. This affords the possibility of avoiding or reducing an additional evaluation, for example in the control and/or in the evaluation unit, and this additionally reduces resources.

The detector can furthermore comprise an optical system, in particular for improving the spatially resolving record. By way of example, this optical system can comprise at least one lens and/or other imaging optical elements and/or further optical elements. By way of example, objectives can also be used for this purpose and image an image region on the test element in the detector, in particular onto the at least one image sensor, by means of one or more lenses. In one embodiment, the imaging region completely acquires the coding.

In a further refinement, as described above, the transfer unit comprises a guide in which the test element with its coding can be guided laterally past the detector. As described above, this guiding past can, for example, be effected manually. However, alternatively, or additionally, the transfer device can also comprise at least one drive apparatus which can be designed to correspondingly move the test element, and would be useful, for example, in the case of test tapes, such as tape cassettes with corresponding test tapes. Thus, the drive apparatus can for example rotate a bad winding of a tape cassette so that the test tape is spooled on.

As illustrated above, the analysis system can furthermore comprise at least one of the described test elements with at least one analysis zone and at least one coding with at least one test element specific item of information and/or at least one position specific item of information. The test element can in particular be a planar test element, with it being possible for the analysis zone and the coding to be arranged on the same side of the planar test element.

The test element can, as is likewise described above, comprise a plurality of analysis zones, for example in the case of a test tape. In the process, as is described above, it is possible for each analysis zone or group of analysis zones to be assigned at least one individual coding. In particular, the analysis zones or the groups of analysis zones and the codings can be arranged on the test element in an alternating fashion, for example alternating along a longitudinal extent of the test tape.

Further refinements of the present invention relate to the type of the coding. Thus, the coding can in particular comprise an optical coding. In particular, this optical coding can comprise a two-dimensional item of optical information, in particular a so-called two-dimensional barcode. The test element specific item of information in particular can be contained in such an optical coding, in particular a two-dimensional item of optical information.

In principle, the shape of the coding and/or the two-dimensional optical information plays a secondary role. By way of example, the coding and/or the two-dimensional item of optical information can have a rectangular geometric shape because rectangular image sensors are also used in many cases. In principle, other geometric shapes are, however, also possible, for example lines, circles, ovals, triangular or differently designed polygonal shapes or the like. Furthermore, it is also possible for provision to be made for random and/or irregular patterns as an alternative, or in addition, to the described shapes.

In particular, the coding can comprise at least one gray-scale coding. Gray-scale coding in this case is intended to be understood as a coding which also utilizes gray values or gray-scale values (these terms are generally used synonymously), i.e. different brightness steps of one or more colors, as information carriers. Depending on the resolution, gray steps between black (in the case of a colorful color, "black" is understood to mean the corresponding darkest step) and white (in the case of a colorful color, "white" is understood to mean the corresponding lightest step) can be effected in the process, such as by implementing discrete steps with one or more intermediate steps between these black and white limit values. By way of example, a gray-scale coding in gray-scale value steps with a constant, predeterminable spacing from black to white can be utilized. However, in principle the term gray-scale value is intended to be understood in broad terms and, for example, also comprises different brightness values in the case of colored detectors.

In order to evaluate the test element specific item of information and/or the position specific item of information a histogram analysis of the gray-scale values can in particular be undertaken in the case where a gray-scale coding is utilized. A "histogram analysis" is in principle to be understood as any analysis which evaluates a frequency distribution. Here, the type of analysis is in principle of secondary relevance, as long as the result represents an assignment of gray values to fill factors or vice versa. Thus, by way of example, a gray value/fill factor evaluation can be undertaken immediately, or else a spatially resolved item of image information can firstly be obtained and then further converted into gray values and fill factors.

An example of a direct, immediate gray value/fill factor evaluation is illustrated in EP 1 843 148 A1. Hence, the histogram analysis can, for example, acquire and evaluate the number of fields and/or pixels within the coding which have a certain gray-scale value. A histogram analysis may be undertaken which comprises a fill factor of individual gray-scale values for a number of fields of the coding instead of a number histogram analysis. Thus, the coding can for example comprise a plurality of fields, for example rectangular or square fields, which are each filled up to an individual fill factor with a certain gray-scale value. By way of example, these fields in the coding can be arranged to form a matrix, for example a rectangular or quadratic matrix. The histogram analysis can then plot the fill factor against the gray value steps, or vice versa, so that in each case pairs of fill factor and gray value or gray-scale value can be formed, which pairs contain the coding. In this fashion, it is possible to assign a number, for example, to a gray-scale coding, and vice versa. Thus the coding can be evaluated by means of a histogram analysis and the at least one item of information contained therein, in particular the test element specific item of information, can be recouped. As explained above, the histogram analysis can at least in part already be performed within the detector, for example in the CCD and/or CMOS chip.

If a gray-scale coding is used, it can furthermore also be used to scale the analysis system. Thus, the gray-scale information can for example comprise a black item of information and/or a white item of information which can be used to scale the detector.

The invention is to be explained in more detail by the following figures and examples.

BRIEF DESCRIPTION OF THE DRAWINGS

The following detailed description of the embodiments of the present invention can be best understood when read in conjunction with the following drawings, where like structure is indicated with like reference numerals and in which.

In order that the present invention may be more readily understood, reference is made to the following detailed descriptions and examples, which are intended to illustrate the present invention, but not limit the scope thereof.

DETAILED DESCRIPTION OF EMBODIMENTS OF THE PRESENT INVENTION

The following descriptions of the embodiments are merely exemplary in nature and are in no way intended to limit the present invention or its application or uses.

Figure 1:
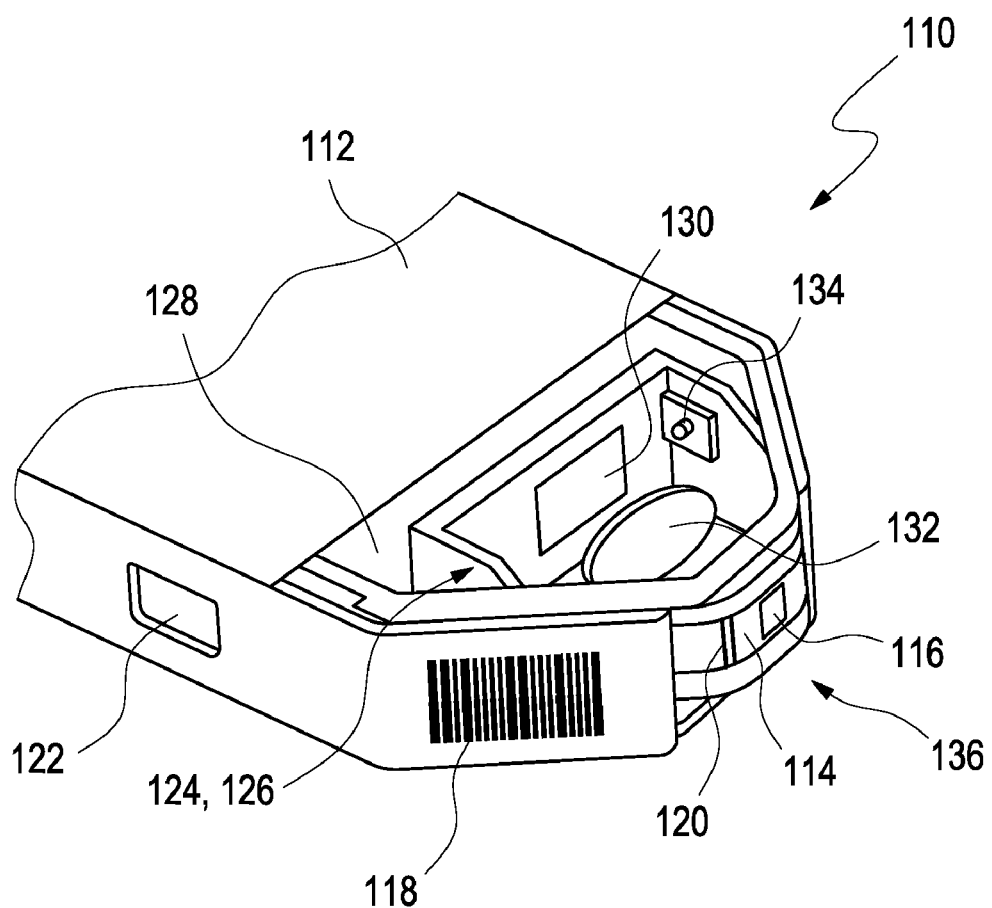
FIG. 1 shows a section of a conventional analysis system with a test tape for optical analyte detections.

FIG. 1 shows a perspective illustration of a section of a known analysis system 110. In the illustrated exemplary embodiment, the analysis system 110 comprises a tape cassette 112, which can be held, for example in a replaceable manner, in a housing (not illustrated) of the analysis system 110. This tape cassette 112 guides a test tape 114 which is only exposed at the tip of the tape cassette 112 and which has a multiplicity of analysis zones 116, spaced apart in the direction of the tape, for the optical detection of glucose in the blood. A coding 118 in the form of a barcode is attached to the outside of the tape cassette 112 and it comprises test element specific information regarding the test tape 114 or the analysis zones 116 and the test chemicals contained in these analysis zones 116.

Furthermore, the test tape 114 comprises positioning markers 120 which can be printed onto the test tape 114 in the form of bars running across the test tape 114 and which, for example, alternate with the analysis zones 116. These positioning markers 120 can for example be acquired by a positioning window 122 in the tape cassette 112 so that spooling the test tape 114 through the analysis system 110 can be controlled correspondingly.

In the illustrated exemplary embodiment, the analysis system 110 furthermore comprises a detector 124 in the form of an optical module 126 which engages into a recess 128 of the tape cassette 112 when the tape cassette 112 is inserted into the analysis system 110. In the illustrated exemplary embodiment, this detector 124 comprises an image sensor 130 for the spatially resolved recording of image information, for example a CCD or CMOS image sensor chip. Furthermore, the detector 124 comprises a spatially resolving optical system 132, for example in the form of one or more lenses. In the illustrated exemplary embodiment, the detector 124 furthermore comprises a light source 134 which can, where necessary, also be provided with an appropriate illuminating optical system and which is designed to illuminate the analysis zone 116 located in a measurement position 136 in the field of view of the detector 124.

The known analysis system 110 illustrated in FIG. 1 thus in each case requires separate detectors or measurement systems for recognizing the position of the test tape 114, for recognizing the coding 118 and for determining the glucose concentration. The division of these measurement-technical objects leads to increased equipment costs and requires installation space.

Figure 2:
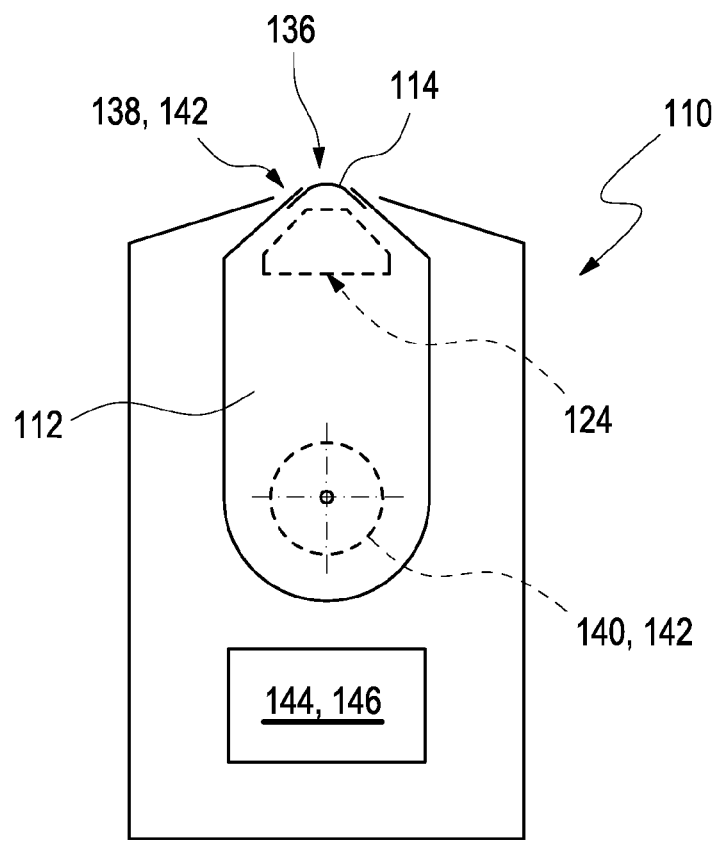
FIG. 2 shows a schematic design of an analysis system according to the invention with a test tape.

The invention therefore proposes that the three mentioned measurement-technical objects are performed by one and the same detector 124. This is illustrated schematically in FIG. 2 on the basis of a first exemplary embodiment of the invention. In principle, the illustrated analysis system 110 can in this case correspond to the analysis system 110 in accordance with FIG. 1 in terms of its design, in which, however, additional detectors for recognizing the coding 118 and an additional positioning sensor (not illustrated in FIG. 1) interacting with the positioning window 122 can be dispensed with. The analysis system 110 once again comprises a tape cassette 112 with a test tape 114 which is only indicated in FIG. 2. The tape cassette 112 provides a guide 138 for the test tape 114 in the region of the measurement position 136, within which guide the test tape 114, which is driven by a drive apparatus 140 which is only generally indicated in FIG. 2, is guided and hence can be positioned relative to the measurement position 136 of the detector 124 (only generally indicated in FIG. 2). The guide 138 and the drive apparatus 140 therefore represent components of a transfer device 142 for positioning the test tape 114.

The analysis system 110 furthermore comprises an evaluation unit 144 which can evaluate the measurement of the blood glucose concentration using the test tape 114 and the detector 124 in order to thus permit a quantitative and/or qualitative analysis of the blood sample. The exemplary embodiment illustrated in FIG. 2 shows that this evaluation unit 144 optionally at least in part comprises components operative as a control 146 which can for example control the tape positioning by means of the transfer device 142. However, in principle, a separate component design is also possible. The evaluation unit 144 and/or the control 146 can in this case comprise one or more electronic components, for example microprocessors and/or other types of electronic components. In addition, one or more input and output units can also be provided, for example interfaces, input pushbuttons, displays, optical and/or acoustic displays or similar apparatuses.

Hence, in the embodiments of the present invention, the detector 124 is utilized in a multifunctional manner. To this end, it is proposed that the coding 118 is not applied to the housing of the tape cassette 112, as is the case in the apparatus illustrated in FIG. 1, but directly onto the test tape 114. However, naturally, it is still possible for an additional coding 118 to be additionally arranged on the housing or at different locations, as is illustrated by way of example in FIG. 1.

Figure 3:
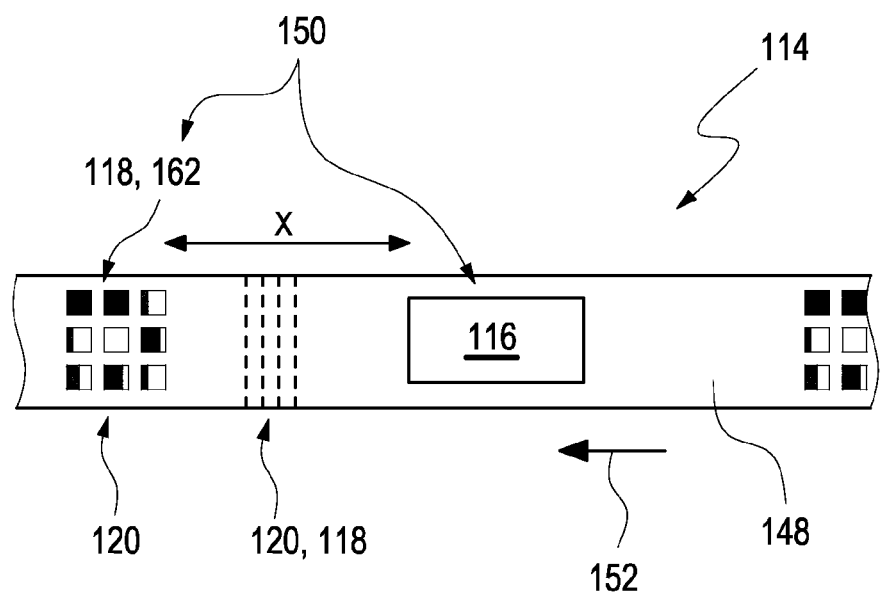
FIG. 3 shows a schematic design of a test tape for use in an analysis system in accordance with FIG. 2.

FIG. 3 illustrates an exemplary embodiment of a test tape 114 which can be used within the scope of the analysis system 110 according to the present invention. Here, only a section of this test tape 114 which alternately comprises analysis zones 116, with test chemicals for detecting the analyte, and codings 118 on a carrier 148, for example a transparent plastic tape, is illustrated. Here, respectively one coding 118 is associated with one analysis zone 116 so that the respective one analysis zone 116 and the associated coding 118 form a coding/analysis zone pair 150. In a spooling direction of the tape, symbolically referred to with the reference numeral 152 in FIG. 3, the coding 118 can for example be stored in front of the analysis zone 116, for example by a known distance X, so that, in the spooling direction 152, the coding 118 of a coding/analysis zone pair 150 firstly passes the measurement position 136, followed by the associated analysis zone 116. However, in principle, other refinements are also possible.

One embodiment of a coding 118 is indicated in FIG. 3 as having a number of individual fields of a two-dimensional coding. However, in principle, a one-dimensional coding, for example in the form of the barcode such as is illustrated in FIG. 1, is also possible to be provided on the test tape 114.

According to one embodiment, an imaging detector 124, such as, for example, a CMOS camera, can recognize the tape position and measure the discoloring of the analysis zone 116 and read the coding 118 itself, particularly if all the information required for this can be recognized simultaneously or sequentially in a measurement window of the detector 124. In particular, it is conceivable in this fashion to apply all required test element specific information and/or position specific information onto the test tape 114 in the form of the optically observable coding 118, for example by printing, labeling or similar application methods. Hence, test element specific information and/or position specific information can be stored individually in the associated coding 118 for each analysis zone 116 or for each group of analysis zones 116 which can simultaneously or sequentially be acquired by the detector 124 in the measurement position 136. In a first position of the test tape 114, the analysis zone 116 or the group of analysis zones 116 are in the measurement position 136 and, by contrast, in a second position of the test tape 114, it is the associated coding 118.

In the exemplary embodiment illustrated in FIG. 3, the coding 118 comprises a coding field 162 for the test element specific information. This coding field 162 can simultaneously be used as a positioning marker and hence also as a carrier of the position specific item of information. However, as is likewise illustrated in FIG. 3 with dashed lines, it is also possible that, alternatively or additionally, provision is made for a separate positioning marker 120 as the carrier of the position specific item of information, analogously to the exemplary embodiment in FIG. 1, for example. This positioning marker 120, which likewise is a component of the coding 118, can for example also be arranged at a predetermined distance from the analysis zone 116 so that the distance X between the coding 118 and the associated analysis zone 116 can for example also be defined from this separate positioning marker 120.

In both cases, that is to say the case in which the coding 118 comprises a separate positioning marker 120 or the case in which the coding field 162 of the coding 118 containing the test element specific item of information is also used for positioning, the detector 124 is able to recognize all elements 116, 118, 120 and can be used to determine the glucose, recognize the position and evaluate the test element specific item of information.

Figure 4:
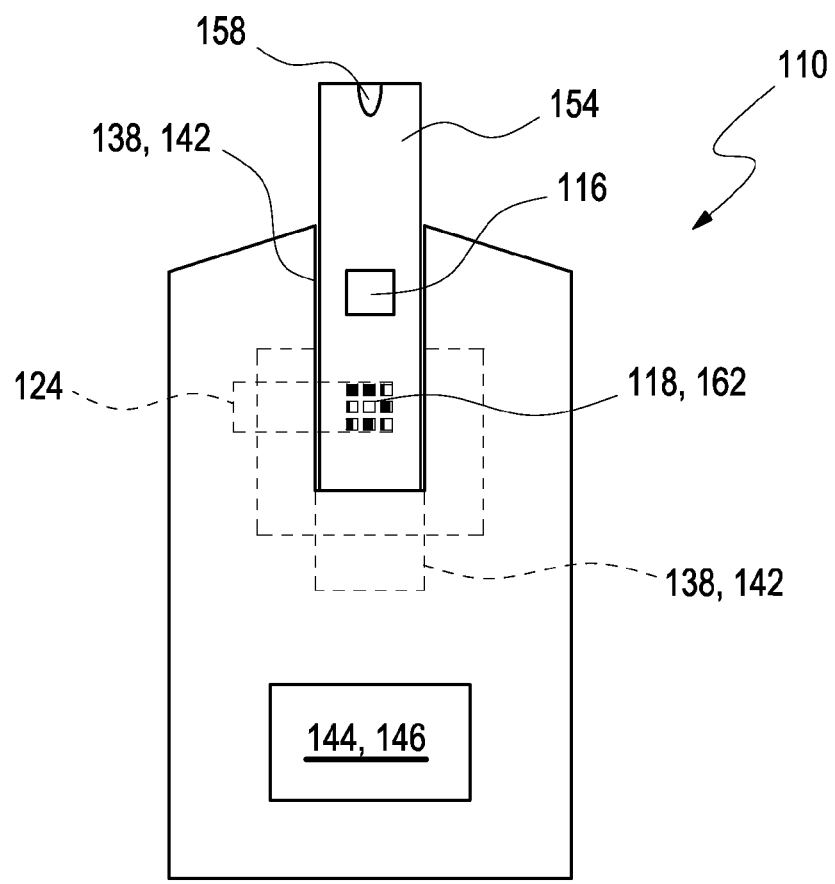
FIG. 4 shows an exemplary embodiment of an analysis system according to the invention with a test strip.
Figure 5:
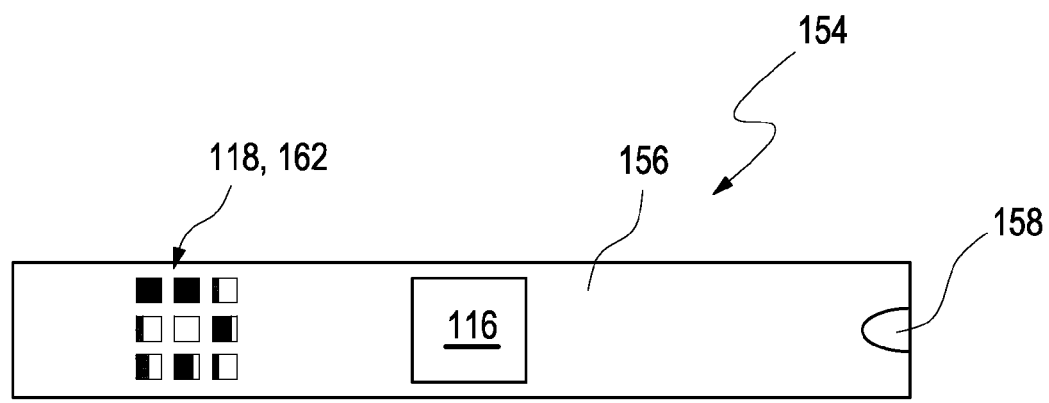
FIG. 5 shows an exemplary embodiment of a test strip for use in an analysis system in accordance with FIG. 4.

The analysis system 110 according to the invention was explained in FIGS. 1 to 3 on the basis of a test element in the form of a test tape 114. FIGS. 4 and 5 illustrate an exemplary embodiment which is based on the use of test strips 154. These test strips 154, which are illustrated individually as an exemplary embodiment in FIG. 5, in turn comprise a carrier 156, for example a paper carrier and/or a ceramics carrier and/or a plastic carrier. This carrier 156 has an application zone 158 at a front end on which a liquid sample, for example a drop of blood, can be applied to the test strip 154. This liquid sample is transported to an analysis zone 116 of the test strip 154 by means of, for example, capillary forces in order to effect an analyte specific reaction which corresponds to the proportion of glucose in the liquid sample at said location.

At one end which in this exemplary embodiment lies opposite to the application zone 158, the test strip 154 furthermore has a coding 118 which contains the test element specific item of information in an encrypted form. In the exemplary embodiment in accordance with FIG. 5 as well, this coding 118 is in turn only generally indicated so that it can for example also comprise a one-dimensional coding, for example in the form of a barcode, in addition to the illustrated two-dimensional coding. The coding 118 is in turn intended to be optically readable. The coding 118 can, furthermore, in turn also comprise one or more positioning markers 120 in addition to the test element specific item of information; this is not illustrated in FIG. 5, but is optionally possible and can ease the positioning. However, alternatively or additionally, the part of the coding 118 comprising the test element specific item of information can simultaneously also be used as positioning marker 120.

In the exemplary embodiment of the analysis system 110 illustrated in FIG. 4, a guide 138 is once again provided as a component of a transfer device 142 for the test strip 154. The effect of this guide 138 is that the test strip 154 can be guided past a detector 124 which is only indicated schematically in FIG. 4. Here, in a second position illustrated in FIG. 4, the coding 118 is wholly or partly arranged in the field of view of the detector 124. If the test strip 154 is pushed further into the analysis system 110, for which purpose the guide 138 can for example be designed in a corresponding elongate fashion, the analysis zone 116 of the test strip 154 enters the field of view of the detector 124, and the test strip 154 is in a first position. The described reaction of the analysis zone 116 can be evaluated in this first position. Otherwise, the functionality of the analysis system 110 in accordance with FIG. 4 can basically correspond to the functionality of the analysis system 110 in accordance with FIG. 2.

Figure 6:
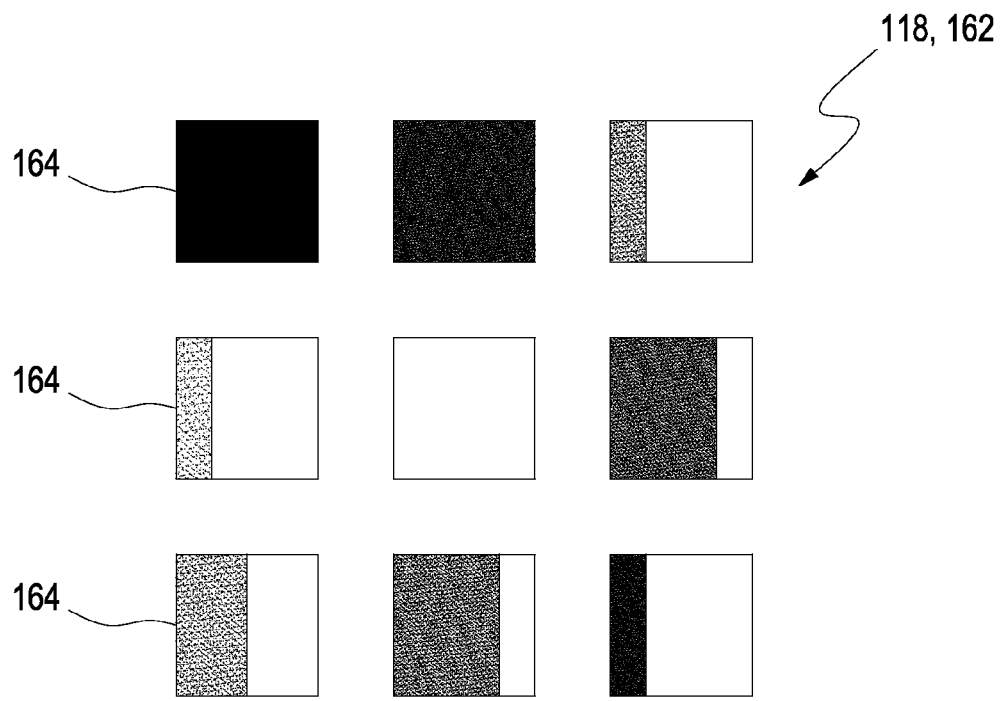
FIG. 6 shows an exemplary embodiment of a coding according to the invention.

FIGS. 6 to 9 show different exemplary embodiments of the coding 118 (or of the part of the coding 118 comprising the test element specific item of information) and examples of a method for its evaluation. Here, FIG. 6 shows an exemplary embodiment of the coding 118 in which the coding 118 comprises a two-dimensional coding field 162. As described above, the coding 118 can additionally also comprise one or more positioning markers 120, or the coding field 162, which comprises the test element specific item of information in encoded form, can simultaneously also be used to position the test tape 114 and/or the test strip 154. The coding 118 illustrated in FIG. 6 can in principle be used on test tapes 114 and test strips 154. However, a coding 118 can also additionally be arranged at different locations, for example on a housing as illustrated in FIG. 1.

According to the invention, the two-dimensional coding by means of the coding field 162 uses the fact that the detector 124 in many cases is fitted as a spatially resolving detector 124 with a spatially resolving image sensor 130, for example in the form of a compact sensor array. The spatially resolved information about the coding field 162 obtained by this detector 124 can for example be used to perform gray value analysis, for example by means of a gray value histogram, for example in a manner analogous to the method described in EP 1 843 148 A1. This histogram generation can for example be implemented directly in the detector 124, for example in a CMOS chip of the detector 124. The advantages in this case are in particular a reduced complexity for the peripheral hardware, i.e. reduced clock times, the possible avoidance of image memory and reduced energy requirements. The advantage, and at the same time the disadvantage, of using such a detector 124 however is the high degree of specialization for a measurement objective. The following explanations now describe a general concept in order to also be able to utilize such a histogram optimized detector 124 for recognizing the coding 118, i.e. to evaluate the test element specific information and/or to evaluate the position specific item of information contained therein, for example to generate a start/stop pulse for the drive apparatus 140. The advantages described above, in particular the reduced complexity for the peripheral hardware, the reduced clock times, the reduction of the memory requirements and the reduction of the energy requirements analogously hold for this embodiment.

Using the example of the coding in FIG. 6, encoding of test element specific information in the coding 118 or the decoding of this information is intended to be described in the following example. In addition to optional additional positioning markers 120, the coding 118 comprises the coding field 162 described above which in the present exemplary embodiment has an at least approximately square shape. The coding field 162 comprises a number of (in this exemplary embodiment nine) fields 164 which in turn can likewise have a square or at least approximately square shape and which are arranged in a 3×3 matrix. The fields 164 can have an edge or be designed without one.

FIG. 6 illustrates that the fields 164 are filled to different fill factors with gray-scale values. This exemplary embodiment of a coding 118 with two-dimensional optical information with gray-scale coding affords the possibility of carrying out a histogram evaluation. To this end, it is possible for an image of the coding 118 or the coding field 162 to be recorded when the test element in the form of the test tape 114 and/or test strip 154 is located in the second position in which the coding 118 is at least in part arranged in the field of view of the detector 124 and hence in the measurement position 136. In this example, the detector 124 can be optimized for an exact determination of gray value distributions. Each gray-scale value can now be assigned a certain number of pixels with this gray value from the fill factor of each individual field 164. In the example, nine gray values are illustrated, each of which being able to take up 4 fill factors, i.e. from completely filled (e.g. the back field in the top left-hand corner) via ¾ filled, ½ filled down to ¼ filled. To clarify the fill factor, the edges of the square fields 164 are still marked in FIG. 6 as well, but this does not have to be the case. Overall, the coding illustrated in FIG. 6 results in 36 combination possibilities (9 gray values×4 fill factors). This only represents one exemplary embodiment of a possible coding. A different number of possible gray-scale values and/or fill factors is also conceivable.

Figure 7:
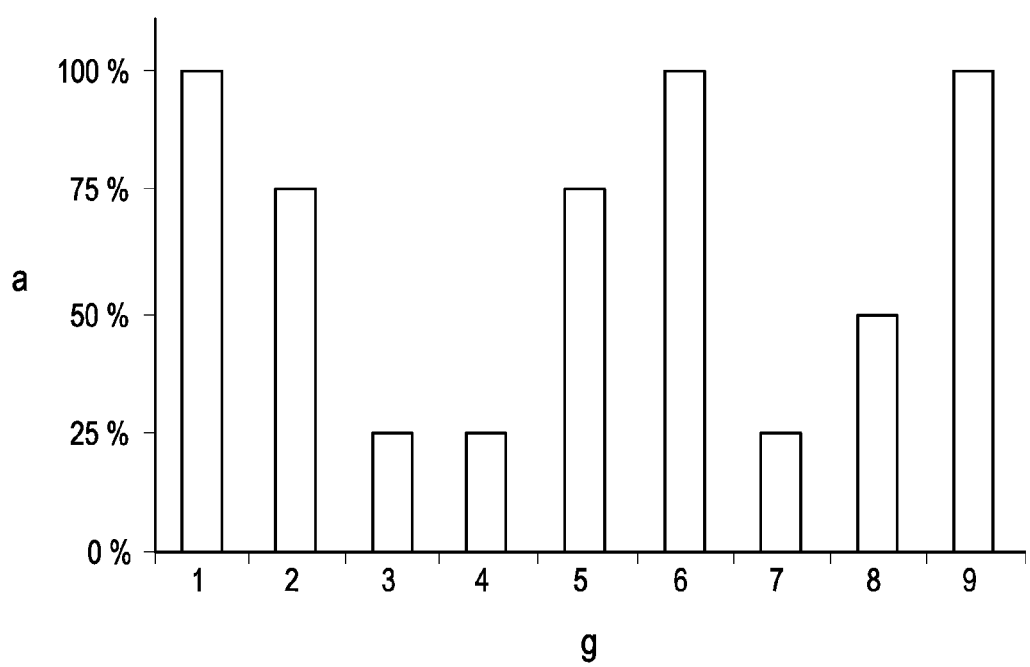
FIG. 7 shows an exemplary embodiment of a histogram analysis of the coding in accordance with FIG. 6.

By way of example, a gray value histogram shown in FIG. 7 would result from the coding 118 illustrated in FIG. 6. In this case, the fill factor in % is plotted above each gray-scale value g, the gray-scale values in this case being numbered through from 1 to 9. If the sequence of the gray-scale values g in the histogram in accordance with FIG. 7 is understood to be an order, i.e. for example a sequence of digits, then it is possible to generate 4⁹=262144 numbers using this 9-field code with 4 fill factors; in order to obtain this with a standardized barcode, for example, a depth of 18 bit would be necessary because 2¹⁸ equals 4⁹.

Figure 8:
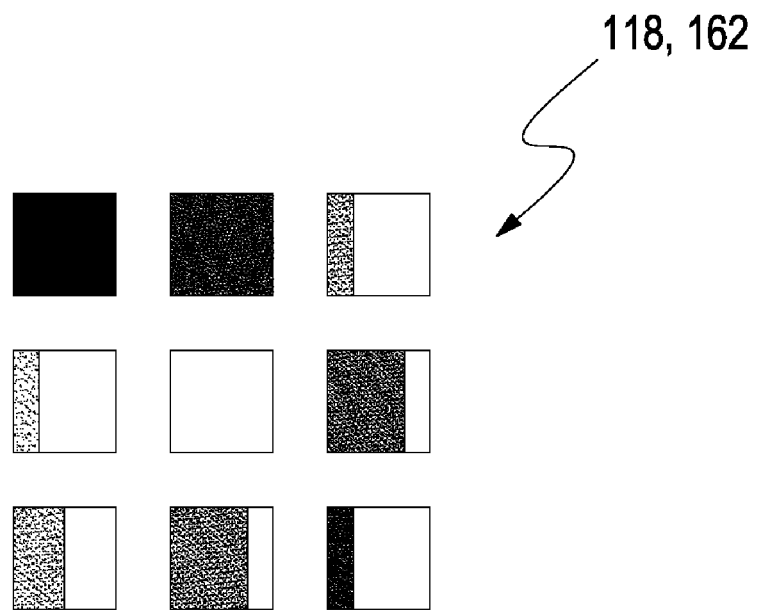
FIG. 8 shows an exemplary embodiment of a gray-scale coding of the number 262144.
Figure 9:
FIG. 9 shows the number 262144 illustrated by a commercial barcode.

As an example, FIGS. 8 and 9 compare the illustration of the number "262144" using the gray value coding (FIG. 8) according to the invention with an illustration using a commercial barcode (Code 25, FIG. 9). The reduction of spatial requirements for a coding at a given line resolution (here 300 dpi) made possible as a result of the extension from 2 (black/white) to 9 gray-scale values can be clearly seen in this case, with it even being possible to significantly reduce the gray value encoding.

Particularly in the case of a gray value coding, it should be stressed the read out by means of a histogram is at least mainly insensitive to translation and rotation. This means that even a tilting of the test strip 154 or test tape 114 makes a read out of the coding 118 possible without any problems. Likewise, the shape of the coding is very flexible so that it is also possible to use horizontally and/or vertically aligned rectangles, circles, diagonal lines with differing gray values and thicknesses, or the like instead of square fields 164 and/or quadratic coding fields 162.

The selection of the 9 gray-scale values with 4 fill factors illustrated in FIG. 6 likewise is a simplified, exemplary illustration. Conceptually, the embodiment of the invention is based on the fact that in analysis systems 110 optimized for glucose determination, the number of recognizable gray values is designed precisely to be able to determine gray values as exactly as possible. This advantage in particular can be utilized for the coding in gray-scale values or for reading these codings 118. While the requirements for the accuracy of the measurement for the glucose determination conceptually typical lie at approximately 0.1% remission in a range of approximately 50% remission, and therefore 500 gray-scale values should be recognizable, it hence seems to be realistic to be able to separately recognize at least 50 gray-scale values for a gray value coding. By way of example, if a detector 124 with an image sensor 130 with 106 pixels is used, 20,000 pixels would be available for each gray-scale value. Assuming a Poisson distribution, the number of pixels of a certain gray value could then theoretically be determined to 0.7% accuracy. Hence, the fill factors could be subdivided into 141 steps. Taking the technical feasibility into account, in particular edge effects and the width of the gray value distribution, it seems to be possible to realize at least 30 steps. Overall, it can be shown that the edge effects for a given area of a rectangle are minimized if the rectangle is a square, as a result of which square fields 164 and/or square coding fields 162 are useful embodiments. Thus, it would be possible to code 5,030 numbers in an image, which corresponds to a binary information depth of approximately 170 bits. If, for example, 406 bits of information are required, the information could thus be illustrated on the detector in at most 3 images.

If the pair of numbers gray value and fill factor are determined, as shown, for example in FIG. 7 on the basis of the histogram analysis, the roles of gray value and fill factor can also be interchanged when coding numbers. Thus, for example, it is possible to order by fill factor rather than have an order by gray values. The gray value can then reproduce the value of this location in the code instead of the fill factor. This even makes it possible to represent 3,050 instead of 5,030 numbers in the above example, which corresponds to a bit depth of 245 bits in a binary system. It can easily be shown, that this change of roles is advantageous whenever the base (originally 50 in this case) of the power is greater than the exponent (originally 30 in this case).

In order to generate the gray values, it is not necessarily required to generate a homogeneous area with a constant gray value, rather differently structured coding fields 162, structured fields 164 or otherwise structured areas can be used as long as the image of the structuring at the location of the detector is significantly smaller than one pixel. Shading and dotting are examples of such structuring.

If appropriate, it is furthermore helpful to use the extreme values black and white, as illustrated by way of example in FIG. 6 in the first field of the first row or in the second field of the second row, not only for reading the coding but at the same time also for scaling the analysis system 110. Once the coding has been read, a histogram of the type illustrated in FIG. 7 then makes it possible to effect a calibration as a reference for determining the glucose concentration by means of the analysis zone 116 on the basis of this black/white information regarding the reference values "black" and "white", in a manner similar to the one currently effected by the separate black and white fields on many tape cassettes. As a result of this calibration, the analysis system 110 can be designed to be more robust against variations in the sensor sensitivity, against a degradation of the illumination light intensity of the light source 134 (for example, the LEDs) or against similar variations.

The gray-scale coding described on the basis of FIGS. 6 and 7 can also be used for only part of the required test element specific information. Thus, for example, the lot coding by means of the coding 118 can be used for only a part of the required code, the remaining part of the coding being able to remain on a different coding medium ("split code"). Thus, for example, an additional coding medium, for example in the form of a barcode on the tape cassette 112, in the form of a ROM key or similar additional coding media can be used.

Figure 10:
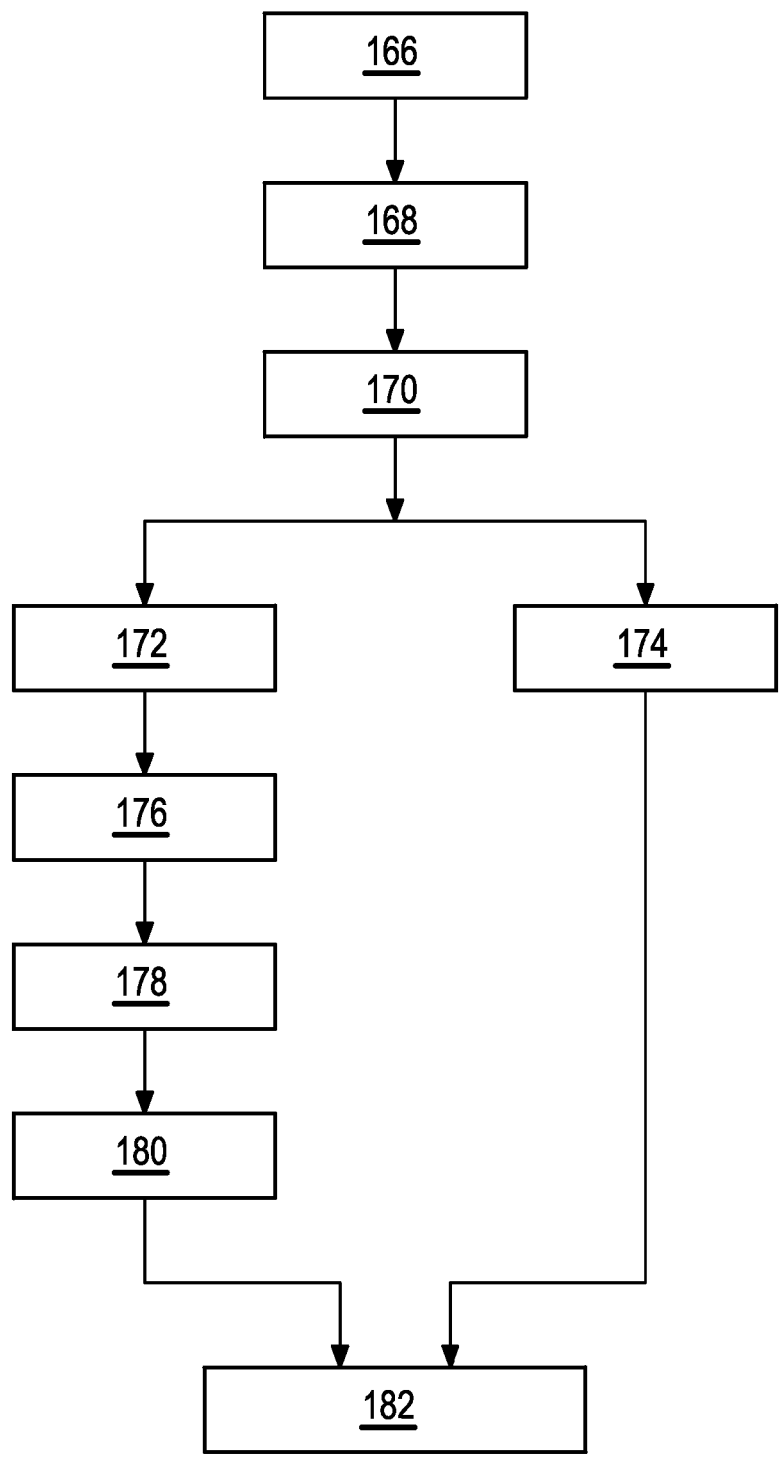
FIG. 10 shows a schematic flowchart of an exemplary embodiment of a method according to the invention.

Finally, FIG. 10 illustrates an exemplary embodiment of a method according to the invention, which comprises the use of the same detector 124 for recognizing the positioning, for evaluating the coding 118 and for evaluating the analysis zone 116 by the same detector 124. This exemplary embodiment of the method according to the invention will be described in the following text using the example of a tape cassette analysis system 110, for example using the analysis system illustrated in FIG. 2. However, in principle, an application to systems with test strips 154 is feasible.

The exemplary embodiment of the method according to the invention is illustrated schematically in FIG. 10. Reference is made to the fact that further method steps not illustrated in FIG. 10 can also be carried out, and that individual or a number of method steps can also be carried out in a repeating fashion, or in a temporally overlapping fashion, or else in a sequence differing from the illustrated one.

The test tape 114 is spooled in a first method step (step 166 in FIG. 10). This can, for example, be carried out until a coding 118 reaches the measurement position 136, that is to say the field of view of the detector 124. There this coding 118 is acquired by the detector 124 (step 168 in FIG. 10).

The coding 118 is then evaluated in step 170. In the exemplary embodiment in accordance with FIG. 10, this evaluation 170 is divided into two and comprises an evaluation of the positioning (step 172) and an evaluation of the test element specific information which is contained in the coding 118 (step 174 in FIG. 10).

In order to evaluate the positioning 172, it is for example possible to recognize separate positioning markers 120 of the coding 118, for example by means of a particular image recognition routine or pattern recognition routine which can be wholly or partly integrated in the evaluation unit 144, the control 146 or in the detector 124. If no separate positioning markers 120 are provided in the coding 118, or in addition to such positioning markers 120, it is also possible to evaluate the position of the coding fields 162 in a similar fashion because the latter can likewise be used as positioning makers 120. This can, for example, also be carried out in turn in an appropriate fashion using image or pattern recognition.

Once this positioning has been evaluated in step 172, the test tape 114 can be correspondingly positioned in method step 176. In the process, the drive apparatus 140 can spool the test tape 114 from the second position, in which the coding 118 is acquired by the detector 124, into a first position, in which the analysis zone 116 is at least in part arranged in the measurement position 136 and hence within a field of view of the detector 124. In this position, a sample can (step 178 in FIG. 10) be assigned to the analysis zone 116 located in the measurement position 136. In the process, the object can be effected by a side lying opposite to the detector 124, the color reaction connected to this application of the sample being able to be observable by the test tape 114 by means of the detector 124, for example. This observation by the detector 124 is signified in general by the method step 180 (measurement) in FIG. 10. The measurement 180 can in general comprise a change of the analysis zone 116 on account of the presence of the at least one analyte in the sample, for example a reaction of detection chemicals with blood glucose. The detector 124 can correspondingly generate signals or measurement specific information or measurement results, which, for example, can comprise one or more images of the image sensor 130.

The evaluation of the measurement effected in step 180 is carried out in method step 182. This evaluation can, wholly or partly, already be effected in the detector 124, for example in the CMOS chip of the image sensor 130, but it can also wholly or partly be carried out in the evaluation unit 144. According to the invention, in the process, the test element specific information 174 contained in the coding 118, obtained in step 174, is utilized in FIG. 10. This evaluation of the test element specific information 174 can for example be effected by means of the method described on the basis of FIGS. 6 and 7, by means of gray value histogram analysis. By way of example, as described above, it is thus possible for fill factor/ gray value number pairs to be formed, in which either the gray value or the fill factor can be used as a base. This affords the possibility of using the gray value analysis to form a number which can comprise the test element specific information. By way of example, the test element specific information can comprise a number of the analysis zone 116 which has just been evaluated so that, for example, a user of the analysis system 110 can be informed about the number of analysis zones 116 still available in the tape cassette 112. Alternatively or additionally, information regarding the evaluation of the measurement can also be added, for example information relating to which discoloring relates to which type of concentration of the analyte to be detected, the lot numbers or the like. This test element specific information is also taken into account during the evaluation of the measurement in method step 182 in accordance with the exemplary embodiment in FIG. 10, so that the greatest possible accuracy of the analysis is available.

The features disclosed in the above description, the claims and the drawings may be important both individually and in any combination with one another for implementing the invention in its various embodiments.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present invention in detail and by reference to specific embodiments thereof, it will be apparent that modification and variations are possible without departing from the scope of the present invention defined in the appended claims. More specifically, although some aspects of the present invention are identified herein as preferred or particularly advantageous, it is contemplated that the present invention is not necessarily limited to these preferred aspects of the present invention.

What is claimed is:

1. An analysis system for detecting at least one analyte in a sample, the analysis system being configured to detect the analyte using at least one test element including one of a test strip and a test tape having at least one analysis zone for detecting the analyte and at least one coding encoded with one or both of at least one test element specific item of information and at least one position specific item of information, the analysis system comprising:
   a detector;
   at least one transfer device configured to enable the detector to acquire the analysis zone in at least a first position and to enable the detector to acquire the coding in at least a second position which differs from the first position;
   wherein the analysis system is configured to acquire at least the test element specific item of information of the coding with the detector when the test element is the test strip; and
   wherein the analysis system is configured to acquire at least the position specific item of information with the detector when the test element is the test tape; and
   wherein in the second position the analysis system is configured to perform a histogram analysis of a gray-scale coding encoded by the coding on the test element to evaluate the test element specific item of information.

2. The analysis system according to claim 1, wherein the analysis system furthermore comprises an evaluation unit operatively connected to the detector and configured to carry out the detection of the analyte using the test element specific item of information.

3. The analysis system according to claim 1, wherein the detector comprises an optical detector.

4. The analysis system according to claim 3, wherein the detector comprises a spatially resolving detector.

5. The analysis system according to claim 1, wherein the transfer device comprises a guide configured for lateral movement of the test element, wherein the at least one coding is configured for moving past the detector during the lateral movement.

6. The analysis system according to claim 1, wherein the transfer device comprises at least one drive apparatus, the drive apparatus being designed to move the test element.

7. The analysis system according to claim 1, furthermore comprising a test element with at least one analysis zone for detecting the analyte and at least one coding with at least one test element specific item of information.

8. The analysis system according to claim 7, wherein the test element comprises a planar test element configured such that the analysis zone and the coding are arranged so as to be acquired by the detector from the same side of the planar test element.

9. The analysis system according to claim 7, wherein the test element comprises a plurality of analysis zones or a plurality of groups of analysis zones, with at least one said coding being assigned to each analysis zone or group of analysis zones.

10. The analysis system according to claim 9, wherein the analysis zones or the groups of analysis zones and the respective codings are arranged alternately on the test element.

11. The analysis system according to claim 7, wherein the coding comprises at least one two-dimensional optical information component.

12. The analysis system according to claim 7, wherein the coding comprises at least one positioning marker provided for encoding the position specific item of information.

13. The analysis system according to claim 1, wherein the histogram analysis comprises a histogram analysis of a fill factor of individual gray-scale values for a number of fields of the coding.

14. The analysis system according to claim 1, wherein the detector is configured to perform the histogram analysis at least in part.

15. The analysis system according to claim 1, wherein the analysis system is furthermore configured to use the gray-scale coding for scaling, the gray-scale coding comprising at least one of a black item of information and a white item of information.

16. The analysis system according to claim 1, wherein the acquisition of the coding by the detector generates at least one item of start information and at least one item of stop information, with the test element comprising a test tape, the analysis system being configured to spool the test tape in accordance with the item of start information and the item of stop information.

17. A method for detecting at least one analyte in a sample comprising the steps of:
- (a) providing an analysis system comprising a test element having at least one analysis zone and at least one coding encoded with one or both of at least one test element specific item of information and at least one position specific item of information, the coding comprising at least one gray-scale coding, a detector, and at least one transfer device configured to enable the detector to acquire the analysis zone in at least a first position and to enable the detector to acquire the coding in at least a second position which differs from the first position, the analysis system being configured to detect the analyte using the test element;
- (b) acquiring the analysis zone in the first position with the detector;
- (c) acquiring the coding in the second position with the detector;
- (d) evaluating the test element specific item of information with a histogram analysis of the gray-scale coding; and
wherein for an analysis system in which the test element comprises a test strip, the coding is encoded with at least the test element specific item of information; and wherein for an analysis system in which the test element comprises a test tape, the coding is encoded with at least the position specific item of information.

18. An apparatus, comprising:
test element for receiving a sample having at least one analyte in the sample, the test element including a plurality of analysis zones or a plurality of groups of analysis zones for detecting the analyte, the test element furthermore comprising at least one individual coding assigned to each analysis zone or group of analysis zones, wherein the coding comprises at least one gray-scale coding encoded with at least one test element specific item of information and the analysis zone and gray-scale coding are configured so that a detector of an analysis system acquires the analysis zone in at least a first position and acquires the gray-scale coding in a second position that is different from the first position and in the second position a histogram analysis of the gray-scale coding can be performed by the analysis system to evaluate the test element specific item of information.

19. The apparatus according to claim 18, wherein the at least one individual coding comprises an individual fill factor of individual gray-scale values.

* * * * *